United States Patent [19]

Vila-Cora et al.

[11] Patent Number: 4,903,706
[45] Date of Patent: Feb. 27, 1990

[54] UNIDIRECTIONAL OCCLUDER

[75] Inventors: Alejandro A. Vila-Cora, Madrid, Spain; Antonio A. Vila-Cora, Houston, Tex.

[73] Assignee: Board of Reagents, The University of Texas System, Austin, Tex.

[21] Appl. No.: 143,660

[22] Filed: Jan. 13, 1988

[51] Int. Cl.$^4$ .............................................. A61B 3/00
[52] U.S. Cl. ................... 128/745; 351/209; 351/45
[58] Field of Search ............... 128/745, 76.5; 350/578, 350/259–262, 640, 642; 351/200–201, 208–209, 218, 245, 45

[56] References Cited

U.S. PATENT DOCUMENTS

| | | | |
|---|---|---|---|
| 742,081 | 10/1903 | Sierle | 351/203 |
| 1,091,701 | 3/1914 | Pixley | 351/203 |
| 1,128,859 | 3/1915 | Zeng | 351/217 |
| 1,169,699 | 1/1916 | Wahlenmaier | 351/202 |
| 1,292,671 | 1/1919 | Allen et al. | 351/202 |
| 1,664,953 | 4/1928 | Tillyer | |
| 2,014,888 | 9/1935 | Forshey | 351/218 X |
| 2,186,206 | 1/1940 | Posner | 351/218 |
| 2,715,352 | 8/1955 | Jobe | |
| 2,726,570 | 12/1955 | Thorburn | 351/218 |
| 3,539,247 | 11/1970 | Broussard | 350/640 |
| 3,588,234 | 6/1971 | Gambs | 351/13 |
| 3,602,581 | 8/1971 | Heine | 351/211 |
| 3,782,364 | 1/1974 | Watt | 128/76.5 X |
| 3,891,311 | 6/1975 | Fletcher et al. | 351/200 X |
| 3,905,688 | 9/1975 | Decker et al. | 351/237 |
| 4,102,564 | 7/1978 | Michael | 351/245 X |
| 4,582,401 | 4/1986 | Grindle | 351/45 |
| 4,610,115 | 9/1986 | Thompson, Jr. | 350/259 X |
| 4,698,564 | 10/1987 | Slavin | 351/158 X |
| 4,756,305 | 7/1988 | Mateik et al. | 128/76.5 X |

FOREIGN PATENT DOCUMENTS 2077946 12/1981 United Kingdom .

OTHER PUBLICATIONS

The New Encyclopedia Britannica, vol. 27, p. 203.
Dorland's Illustrated Medical Dictionary, 27th Edition, 1988, p. 1457.

*Primary Examiner*—Angela D. Sykes
*Attorney, Agent, or Firm*—Arnold, White & Durkee

[57] ABSTRACT

The present invention relates to an improved device for use in the detection and identification of various misalignment conditions of the eye, for example heterophorias, strabismus and the like. The device, in its preferred embodiment, includes a unidirectional occluder having an occluding disk which occludes an individuals sight in one direction through the disk while allowing direct observation of the occluded eye from the other side of the disk. Preferred embodiments include a self contained hand held support having a handle region and an occluder region, the occluder region being of the size effective to occlude vision of a fixation target through one or both eyes, the disk formed of a reflective transparent material mounted within the occluder region, a light source positioned on one side of the disk so as to illuminate the side of the disk when energized, and a mechanism contained within the support for energizing the light source, the energizing mechanism including a switch mounted on the support.

15 Claims, 1 Drawing Sheet

UNIDIRECTIONAL OCCLUDER

BACKGROUND OF THE INVENTION

1. Field of the Invention

The present invention relates generally to devices having particular utility in the diagnosis and treatment of conditions of the eye. In particular, the invention relates to devices useful as ophthalmologic occluders to assist in the diagnosis of various conditions of the eye, such as stabismus, heterophorias, cyclophorias and the like.

2. Description of the Related Art

Conditions of the eye involving muscular imbalances or misalignments, such as manifest deviations (heterotropias) or latent deviations (heterophorias), are fairly common disorders which can be treated through the use of appropriate corrective devices or therapeutic maneuvers. Unfortunately, the existence of the condition may not be readily apparent to the afflicted individual, such as where the condition is latent or in early stages of progression. Identification and correction of such problems are made even more difficult by the fact that their diagnosis typically involves a fair degree of subjective physician skill as well as familiarity with the signs of the condition, signs which are often difficult to discern or recognize.

Latent strabismus, or heterophoria, is a condition involving a latent misalignment of the eyes. One test commonly employed by physicians to identify latent strabismus is the so-called "cover test". In the cover test, one of a patient's eyes is covered or "occluded" and the patient is asked to look at or "fix" on a particular point using his other eye. When the cover or occluder is removed, the misaligned eye often makes a readjustment movement that is distinctive of the particular defect; e.g., a "fusional" movement in the case of heterophoria, or a "refixation" movement in the case of a manifest deviation. To induce the refixation movement, the occluder often needs to be repositioned to cover the fellow eye.

Unfortunately, when conventional occluders are used the cover test method requires a fairly high degree of experience and ability from the observer, in that the readjustment eye movements are often quick and difficult to discern. The difficulty is compounded by the fact that the occluder itself tends to obscure the observers ability to see certain eye movements. For example, if a latent strabismus exists, the occluded eye moves in a distinctive fashion but these movements are obscured by the occluder and thus go unnoticed by the observer.

Moreover, certain alignment deviations can't be diagnosed readily through the use of the conventional cover test. For example, in the case of cyclophoria, a latent rotational stabismus in which the eye moves around an anterior/posterior axis, the eye movement is of a very small amplitude. Where a conventional occluder is employed, these small movements are not generally discernable. For this reason, the diagnosis of cyclophoria has generally required complex instrumentation, subjective diagnostic techniques or both.

One type of occluder which has been designed in an attempt to address these problems is the so-called frosted glass occluder. As the name implies, the frosted glass occluder employs partially opaqued frosted glass in place of an entirely opaque occluding surface. However, the frosted glass occluder has not met with much success. This is because although the frosted glass appears to do a fairly good job as a conventional occluder, it suffers from many of the same drawbacks as the conventional occluder—the frosted glass tends to obscure the observers view to a significant extent, making the instrument virtually useless for detecting conditions where a transparent rather then translucent view of the eye is needed to detect fine eye movements.

Various other methods and devices are known which are used as an aid in the diagnosis of latent or manifest strabismus. One such device, the "Maddox Rod", is a instrument used to estimate or measure the type or the amount of an ocular misalignment based on the information given by the patient. It is an instrument that measures the subjective deviation. Other devices such as the synoptophore, can be used to determine the type and amount of an occluder misalignment both in subjective and in objective ways. Unfortunately, these devices and methods are either highly subjective in nature or involve complex and expensive instruments. In any event, none of these instruments allow direct detailed observation of the eye through the occluder while the eye is in an occluded state.

The problems enumerated in the foregoing are not intended to be exhaustive but rather are among many which tend to impair the effectiveness of previously known methods and devices for testing for misalignment of the eyes. Other noteworthy problems may also exist; however, those presented above should be sufficient to demonstrate that the prior devices and techniques appearing in the art have not been altogether satisfactory.

SUMMARY OF THE INVENTION

Recognizing the need for improved methods and devices for the diagnosis of misalignment and related muscular conditions of the eye, it is, therefore, a general object of the present invention to provide a novel occluder which minimizes or reduces at least some of the problems previously noted.

It is a further object of the present invention to provide a device that is inexpensive and simple to use and yet which does rely on subjective responses of the patient to the same degree as prior devices.

It is a more particular object to provide an occluder device which allows the practitioner to comfortably observe in detail an individual's eye through the occluder while the eye is in its occluded state.

It is still a further object of the invention to provide a device which allows a practitioner to diagnosis heterophorias and cyclophorias, which have previously been diagnosed only with difficulty.

It is yet a further object of the invention to provide a device that is a self contained hand held instrument, readily transported by a practitioner without need for bulky or complex instrumentation.

Accordingly, in its most general and overall scope, the present invention is directed to an apparatus which includes a support and a means, connected to the support, for occluding at least one eye of an individual while permitting observation of the occluded eye. As used herein, the term "occlude" refers to the action of covering an individual's eye to restrict his vision in a manner that prevents the individual from seeing through the occluded eye, a target that is being seen through the fellow eye. Thus, the term occluded eye refers to an eye which is covered by an instrument in such a way that the instrument prevents the individual from seeing a target by means of the occluded eye, while such target is being seen by the individual through the fellow, non-occluded eye.

In more particular embodiments of the invention, the occluding means comprises a disk mounted on the support, the disk formed of a reflective transparent material; and means connected to the support for opaquing one side of the disk relative to the other. As used herein, the phrase "reflective transparent material", refers to a material which both reflects light and transmits light. That is, the material is such that incident light directed towards a surface of the material, such as a surface of a mounted disk, will tend to reflect the incident light as well as transmitting a portion of the incident light through the disk. An exemplary reflective transparent material are materials such as those commonly employed in the production of two-way mirrors and the like. When these reflective transparent materials are used to construct lenses, sheets, panes or the like, and one side of the sheet or pane is illuminated to a greater extent than the other side, the illuminated side appears as a mirror and is thus "opaqued" relative to the other side. Alternatively, when one views the reflective transparent material from the non-illuminated side, it appears transparent and the viewer can observe objects on the illuminated side through the pane from the non-illuminated side.

Accordingly, the opaquing means will preferably comprise a light source connected to the support such that when illuminated, one side of the disk will be illuminated, thus opaqued, on one side of the disk relative to the other. Most conveniently, the light source will be positioned on an axially extending flange located along a circumferential portion of the disk, such that the light source is juxtapositioned adjacent a surface of the disk.

However, there is no strict requirement that a light source be actually affixed to the apparatus. All that is required is that one side of the disk be illuminated relative to the other. This can be accomplished generally by providing a light source, preferably directed towards the surface of the occluder disk to be opaqued, or alternatively directed towards the patient's eye.

The size, shape and thickness of the occluding disk is not particularly crucial. All that is required is that the disk be of a sufficient size to allow the practitioner to use the disk to occlude vision. In a broad sense, therefore, the disk will generally have a diameter of on the order of 15 or so millimeters up to as large as, for example, a patient's face. The smaller size is generally limited by the size of an individuals pupil whereas the larger size is generally bounded by what is practical. The more preferred sizes will be on the order of 2 cm to 12 cm, with about 7 cm being most preferred. The thickness of the disk is also not particularly crucial and will generally depend on the type and amount of reflective transparent material employed in its preparation. Moreover, the disk may be of virtually any shape, for example, rectangular, circular, annular, oblong, etc., so long as it serves the function of occluding vision.

In certain embodiments, the apparatus of the invention will preferably include a means attached to the support for positioning the occluding means over the eye. Useful positioning means will include, for example, a handle, where the apparatus is one intended for hand held, self contained use. However, usefulness of the present invention is not limited to hand held devices and other positioning means may include, for example, straps, goggles, frames, glasses, helmets, devices held distant from the patient and the like.

In certain preferred embodiments, the reflective transparent material, defined in a functional sense, will reflect at least about 30% light, while transmitting at least about 5%, of incident light. Where at least about 30% of incident light is reflected, it will be appreciated that one side of a disk made of such material can be readily opaqued by the reflection of incident light thereon. Moreover, transmission of at least about 5% of incident light will allow an observer on the non illuminated, non opaqued side of such a disk to readily view objects through the disk material.

In more preferred embodiments, however, the reflective transparent material will reflect at least about 60% of incident light, while transmitting at least about 10% of incident light.

In still further preferred embodiments, the reflective transparent material will reflect about 80% and transmit about 20% of incident light.

Of course, it is not necessary that the entire surface of the opaguing means be constructed of the reflector transparent material. All that is required is the sufficient portion of the disk be so constructed so as to allow an observer to see through a sufficiently sized window to allow observation of, for example, the occluded eye. Thus, for certain application it may be desirable to form only a central or "bull's-eye" portion of the disk while leaving the remainder portion of the disk formed of a fully opaqued, nontransparent material. The opposite construction may be desirable for certain other applications, forming a central disk made of a fully opaque, nontransparent material and leaving the surrounding made of the reflective transparent material.

A useful reflective transparent material which may be used in connection with the present invention is known in the art as aluminum-polyester reflective film. This material, also known as reflective window film or metalized polyester film, is readily available, for example, as sold by Madico Film (Woeburn, MA). One of the Madico Film metalized polyester film products, sold under the trademark RS220X, will work well in the practice of the present invention. The RS220X film is approximately 1 mil. thick and transmits about 16% of incident light (at 550 nm) while reflecting about 84%. Other uses of this material, as discussed above, include the preparation of two-way mirrors, tinting of automobile and other types of windows, and the like.

For the preparation of useful disks in accordance herewith it may be desirable to mount sheets of aluminum-polyester between layers of transparent materials such as glass or plastic. This can be accomplished by simply layering sheets of the aluminum-polyester material between transparent layers of glass or plastic, wherein the number or thickness of the aluminum-polyester sheet(s) will determine the overall reflective/transmittance parameters of the disk. For example, certain commercially available aluminum-polyester sheets (Madico Film, Woeburn, MA) are believed to have a reflective index of about 60 to about 95% of incident light. Where one combines multiple layers of such a material, the reflective behavior will be increased proportionally. Thus, for example, where one employs two sheets of aluminum-polyester, where each sheet reflects about 80% of incident light, a total reflective index of about 96% will be obtained (i.e., 80%+(80% of 20%)).

As mentioned, the transparent layers, where employed, will typically comprise glass or plastic. While planoglass or plastic will generally be the norm, the use of lenses, such as convex or concave lenses, is not excluded. Moreover, the use of lenses having a magnifying, refractive or prosmatic effect may be particular useful in certain instances, for example, where the examined eye has a significant refractive error.

In its most preferred embodiment, the apparatus of the present invention will include:

(a) a self-contained hand-held support defining a handle region and an occluder region, the occluder region being of a size effective to occlude vision;

(b) a disk formed of a reflective transparent material mounted within the occluder region;

(c) a light source positioned on one side of the disk so as to illuminate the side of the disk when energized; and (d) means contained within the support for energizing the light source, the energizing means including a switch mounted on the support.

As used herein, the phrase "self-contained handheld" housing refers to a housing of a size which may be readily transported and used in one or both hands, without the need for cumbersome attachments or use of outside receptacles such as, for example, plugging into a wall. This is achieved, for example, by providing a housing which includes a self-contained energizing source such as batteries or the like, to allow illumination of one side of the disk through the use of a light source positioned on one side of the disk.

Examples of the more important features of this invention have thus been summarized rather broadly in order that the detailed description thereof that follows may be better understood, and in order that the contribution to the art may be better appreciated. There are, of course, additional features of the invention that will be described hereinafter and which will also form the subject of the claims appended hereto.

These and other objects, features and advantages of the present invention will become apparent with the reference to the following detailed description of the preferred embodiment thereof in connection with the accompanying drawings wherein like reference numerals have been applied to like elements.

DETAILED DESCRIPTION OF A PREFERRED EMBODIMENT OF THE INVENTION

Figure 1:
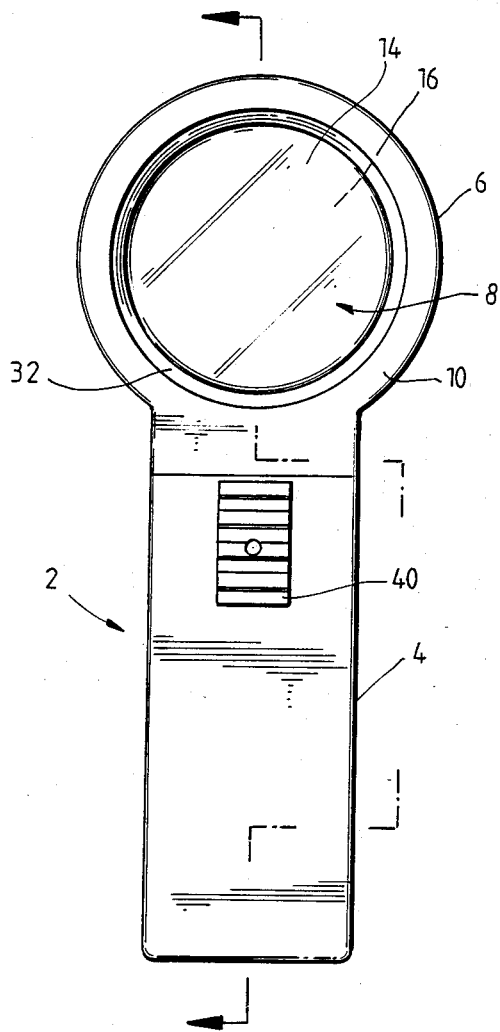
FIG. 1 is a plan view of a preferred device in accordance with the present invention.

Turning now to the figures, there is shown in FIG. 1 a typical apparatus in accordance with the present invention. The apparatus includes a self-contained handheld support 2 defining a handle region 4 and an occluder region 6. The occluder region includes an occluding means 8 mounted with an annular frame 10. The occluding means 8 includes a disk 12 mounted within the annular frame 10 on the support 2.

The handle 4 is elongated in form and more or less rectangular in shape. The occluder region 6 is generally an extension of the handle 4 and presents a form preferably cylindrical with its axis being perpendicular to the axis of the handle 4. The occluder region 6, being annular in shape, is completely hollow and open through both sides, thus presenting an opening to both sides 14, 16 of the disk 12.

As depicted in the figures, the disk 12 includes an aluminum-polyester layer 20 sandwiched between two layers of plano-glass 22, 24. The aluminum-polyester layer 20 is comprised of two aluminum-polyester sheets 26, 28. The disk 20 is mounted in such a way that it fits precisely in the interior surface of the annular frame 10. The disk 20 is held in place by the outside of the annular frame 10, being sandwiched between two annular retention members 30, 32.

Figure 2:
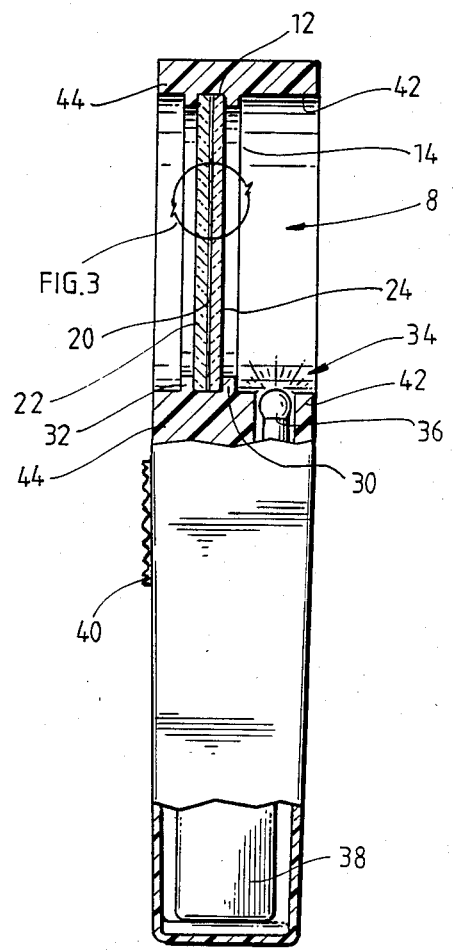
FIG. 2 is a partial cross-sectional side view along the line of 2—2 of the device shown in FIG. 1.
Figure 3:
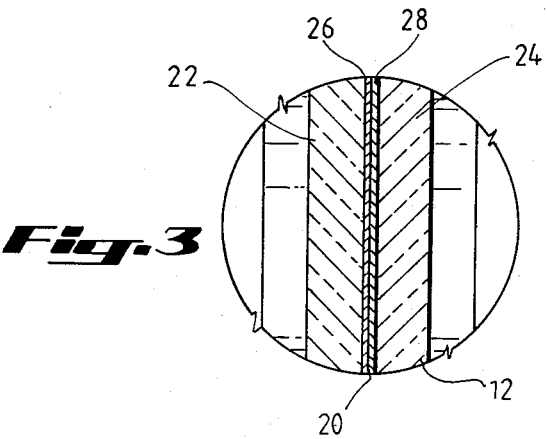
FIG. 3 is a close up cross-sectional of the vieW labeled 3 of FIG. 2.

Shown in FIG. 2 is a means for opaquing one side of the disk relative to the other, the opaquing means 34 being depicted in terms of a light source 36, an energizing means in the form of a battery 38 and switch 40. It has been found that a 2.2 V light bulb and two 1.5 V batteries work well in this regard.

As will be appreciated, the annular frame 10 of the support 2 defines axially extending annular flanges 42, 44 which extend axially along a circumferential portion of the disk 12. One of the axially extending flanges, flange 42, is preferentially slightly larger than the other flange 44, in order to accommodate positioning of the light source 36 in a position juxtaposed and adjacent to a surface of the disk 12. As depicted, the light source 36 is recessed into the flange 42 in order to allow illumination of one side 14 of the disk 12.

Through use of an apparatus the foregoing type, it is possible to make a quick diagnosis of latent strabismus thanks to the occluding means of the present invention. The combination of the aluminum-polyester sheets, and the illumination source, allow a quick, simple and easy medical examination for heterophorias, this condition consisting of a tendency for the eye to deviate and misalign. The condition is latent in that it does not become manifest as long as both eyes are seeing the same image, but does become manifested when one eye receives an image different from the other eye.

Thus, diagnosis is achieved by positioning the occluding means in front of the eye in a manner to occlude it, and actuating the means such that one side of the disk, i.e. the illuminated side, is rendered opaque while the side of less illumination, i.e. the non illuminated side, is rendered transparent. Thus, when the light is energized, and the illuminated side of the occluder is positioned over the eye, the patient's vision is occluded whereas an observer can directly view the occluded eye through the transparent side. In other words, with this device it is possible to perform the "cover test" for the diagnosis, but with the advantage that the examiner can maintain constant observation in the position or movements of the occluded eye, allowing a greater perception of diagnostic eye movements which would not otherwise be as easily apparent through the use of occluders of the prior art.

In use, a low room illumination is preferable. The device is positioned over a patient's eye with the occluder light turned on, and the patient is requested to direct the attention through the unoccluded eye towards a fixation target. This allows the examiner to directly observe the occluded eye while the patient's view is significantly attenuated through the covered eye. Heterophoria becomes apparent as disruption of fusion occurs. The device can then be used as a conventional occluder by removing the occluder, or turning off the light, and observing the uncovered eye for a fusional or a refixation movement.

The device may also be used for diagnoses of manifest deviations as in the case of heterotropia. In the case of a heterotropic individual, the practitioner observes a distinct refixational movement as the eye returns from its misaligned position to its aligned position. For the detection of the amount of heterotropia plus the amount of heterophoria, an alternate cover test may be employed wherein the device of the present invention is moved back and forth from the right to the left eye, and the position and movement of each eye are observed. The occluder may be used in conjunction with grids and/or prisms to quantitate the ocular misalignment. The prisms may be incorporated with the occluder or may be used as an independent tool in addition to the occluder.

For the diagnosis of conditions not previously amenable to the cover test, such as in the case of cyclotropia or cyclophoria, the device is positioned over the individual eye and the opaguing means is turned on and off to see the response of the tested eye. Where cyclophorias or cyclotropias are present, the observer will see tortional movements of the eye around an anteroposterior axis. Observation may be enhanced by means of magnifying adds, which may be incorporated into the occluder or used as an independent tool in addition to the occluder.

Through use of the present invention, the practitioner will typically realize one or more advantages. For example, an examination performed by an ophthalmologist, optometrist or orthoptist will typically be performed in a very simple way that is quick, efficient and convenient due to the small size of the support itself. As mentioned, the device also allows direct observation of the eye while the eye is occluded thus allowing determination as to whether or not the eye has deviated without the need to look for the very quick movement of the eye to its original position when the eye is uncovered. This allows one to observe details of the deviated eye by comparing the observation with and without the occlusion, making it possible to determine whether or not heterophoria or other types of strabismus is present.

The foregoing description of the invention has been directed to a particular preferred embodiment in accordance with requirements of the patent statutes and for purposes of explanation and illustration. It will be apparent, however, to those skilled in the art that many modifications and changes in both apparatus and method may be made without departing from the scope and spirit of the invention. For example, while a self contained hand held device is preferable for most applications, there is no reason why the opaquing means of the present invention cannot be arranged in different, less mobile supports so long as the general nature of the invention is maintained. Also, it would be further apparent that alternative arrangements of the disk, including construction and materials forming the various layers of the disk, can be utilized without departing from the spirit of the invention. For example, those of skill in the art will appreciate that a number of suitable modifications may be made in this regard. These, and other modifications of the invention will be apparent to those skilled in the art. It is applicant's intention in the following claims to cover all such equivalent modifications and variations which fall within the true spirit and scope of the invention.

What is claimed is:

1. An ophthalmologic occluder apparatus comprising:
   (a) a support; and
   (b) means, connected to the support, for occluding at least one eye of an individual while permitting observation of ocular movements of the occluded eye, said occluding means including—
      a disk mounted on the support, the disk formed of a reflective transparent material and having two sides; and
      means connected to the support for opaquing one side of the disk relative to the other.
2. The apparatus of claim 1 further comprising means attached to the support, for positioning the occluding means over the eye.
3. The apparatus of claim 2 wherein the positioning means comprises a handle.
4. THe apparatus of claim 1 wherein the opaquing means comprises a light source connected to the support.
5. The apparatus of claim 4 wherein the support defines an axially extending flange along a circumferential portion of the disk and the light source is positioned on the flange.
6. The apparatus of claim 1 wherein the reflective transparent material reflects at least about 30%, while transmitting at least about 5%, of incident light.
7. The apparatus of claim 1 wherein the reflective transparent material reflects at least about 60%, while transmitting at least about 10%, of incident light.
8. The apparatus of claim 1 wherein the reflective transparent material reflects about 80% and transmits about 20% of incident light.
9. The apparatus of claim 1 wherein the reflective transparent material comprises an aluminum-polyester layer.
10. The apparatus of claim 9 wherein the disk comprises aluminum-polyester mounted between transparent layers.
11. The apparatus of claim 10 wherein the transparent layers comprise glass or plastic.
12. An apparatus comprising:
   (a) a self-contained hand-held support defining a handle region and an occluder region, the occluder region being of a size effective to occlude vision through one or both eyes;
   (b) a disk formed of a reflective transparent material mounted within the occluder region, said disk having two sides;
   (c) a light source positioned on one side of the disk so as to illuminate the side of the disk when energized; and
   (d) means contained within the support for energizing the light source, the energizing means including a switch mounted on the support.
13. A method for the detection of strabismus in a patient suspected of having such a condition, the method comprising the steps of:
   (a) placing a disk formed of a reflective transparent material mounted in an occluder device in front of at least one eye of a patient;
   (b) occluding the patient's vision in at least one eye through the use of the device;
   (c) observing the occluded eye to detect an ocular movement.
14. The method of claim 13 wherein only one eye is occluded, the method comprising fixing the vision of the unoccluded eye on a specified point.
15. The method of claim 13 wherein said occlusion of the patient's vision is achieved by illuminating the side of said disk closest to the patient's eye.

* * * * *